United States Patent
Kang et al.

(10) Patent No.: US 7,632,968 B2
(45) Date of Patent: Dec. 15, 2009

(54) METHOD FOR PRODUCING (METH) ACRYLIC ACID

(75) Inventors: Seong Pil Kang, Daejeon (KR); Seok Hwan Choi, Daejeon (KR); Kyoung Su Ha, Daejeon (KR); Jun Seok Ko, Seoul (KR); Young Bae Kim, Yeosu-si (KR); Boo Gon Woo, Daejeon (KR); Min Jeong Park, Jeonju-si (KR)

(73) Assignee: LG Chem, Ltd. (KR)

( * ) Notice: Subject to any disclaimer, the term of this patent is extended or adjusted under 35 U.S.C. 154(b) by 69 days.

(21) Appl. No.: 11/192,223

(22) Filed: Jul. 28, 2005

(65) Prior Publication Data

US 2006/0025629 A1 Feb. 2, 2006

(30) Foreign Application Priority Data

Aug. 2, 2004 (KR) .................. 10-2004-0060909

(51) Int. Cl.
 *C07C 51/42* (2006.01)
(52) U.S. Cl. ..................................... 562/600
(58) Field of Classification Search ................ None
 See application file for complete search history.

(56) References Cited

U.S. PATENT DOCUMENTS

| | | | | |
|---|---|---|---|---|
| 3,717,675 A | 2/1973 | Sennewald et al. | ...... | 260/530 N |
| 3,921,150 A | 11/1975 | Silcox | ............... | 91/4 |
| 3,932,500 A | 1/1976 | Duembgen et al. | ...... | 260/526 N |
| 4,554,054 A | 11/1985 | Coyle | ................ | 203/15 |
| 6,498,272 B1 * | 12/2002 | Schroder et al. | ............ | 562/600 |

FOREIGN PATENT DOCUMENTS

| | | |
|---|---|---|
| CN | 1296470 A | 5/2001 |
| DE | 3429391 | 2/1985 |
| EP | 0009545 A1 * | 4/1980 |
| EP | 0 009 545 | 12/1982 |
| EP | 0 297 788 A2 | 1/1989 |
| EP | 1 026 145 A2 | 8/2000 |
| GB | 1 293 848 | 10/1972 |
| GB | 1 466 209 | 3/1977 |
| JP | 51-25602 | 2/1976 |
| JP | 61-218556 | 9/1986 |
| JP | 62-096447 | 5/1987 |
| JP | 64-006225 | 1/1989 |
| JP | 64-006232 | 1/1989 |
| JP | 09-157213 | 6/1997 |
| JP | 2001-226320 | 8/2001 |
| JP | 2003-238485 | 8/2003 |

OTHER PUBLICATIONS

Korean Intellectual Property Office, International Search Report dated Sep. 27, 2005.
People's Republic of China; Office Action; Sep. 5, 2008.
Supplementary European Search Report in regards to Application No./ Patent No. 05780776.0-1211; Dated : Jul. 16, 2008.

* cited by examiner

*Primary Examiner*—Paul A Zucker
(74) *Attorney, Agent, or Firm*—Cantor Colburn LLP

(57) ABSTRACT

Disclosed is a method for producing (meth)acrylic acid comprising a process of recovering (meth)acrylic acid as aqueous (meth)acrylic acid solution from a (meth)acrylic acid-containing gas mixture produced by the catalytic gas phase oxidation of at least one reactant selected from the group consisting of propane, propylene, isobutylene and (meth) acrolein, wherein the recovering process comprises the steps of: (1) feeding the (meth)acrylic acid-containing gas mixture into a quenching tower and condensing it in the quenching tower so as to recover an aqueous (meth)acrylic acid solution from the bottom of the quenching tower, in which some of the recovered aqueous (meth)acrylic acid solution is recycled to the upper portion of the quenching tower so as to condense the (meth)acrylic acid-containing gas mixture; (2) passing the uncondensed part of the (meth)acrylic acid-containing gas mixture from the top of the quenching tower to a distillation tower; and (3) heating the bottom of the distillation tower to separate water-containing impurity components from the uncondensed (meth)acrylic acid-containing gas mixture and to discharge them from the top of the distillation tower. A system used for carrying out the method is also disclosed.

12 Claims, 4 Drawing Sheets

METHOD FOR PRODUCING (METH) ACRYLIC ACID

BACKGROUND OF THE INVENTION

1. Field of the Invention

The present invention relates to a method for producing (meth)acrylic acid. More specifically, the present invention relates to a method for producing (meth)acrylic acid using a process of recovering (meth)acrylic acid as aqueous (meth) acrylic acid solution from a (meth)acrylic acid-containing gas mixture produced by the catalytic gas phase oxidation of at least one reactant selected from the group consisting of propane, propylene, isobutylene and (meth)acrolein.

2. Description of the Prior Art

Conventionally, (meth)acrylic acid is obtained by the partial oxidation of propane, propylene, isobutylene and/or (meth)acrolein with a heterogeneous oxidation catalyst in the presence of water vapor. In this oxidation method for producing (meth)acrylic acid, by-product impurities, such as water or unreacted propane, propylene, isobutylene and (meth)acrolein, acetic acid, formic acid, formaldehyde, acetaldehyde, maleic acid, propionic acid, furfural and the like, are generated. A (meth)acrylic acid-containing gas mixture containing such by-product impurities is generally collected as (meth) acrylic acid solution via contact with an absorption solvent, and the solvent is separated by distillation, etc. Then, low-boiling point and high-boiling point components are selectively separated.

Methods for recovering (meth)acrylic acid from (meth) acrylic acid-containing gas by an absorption solvent, which have been known till now, can be broadly divided into methods using an organic solvent (e.g. U.S. Pat. Nos. 3,932,500 and 6,498,272) and methods using water or aqueous solution as solvent (e.g. Japanese Patent Publication No. Sho51-25602 and Japanese Laid-Open Patent No. Hei9-157213). Such recovering methods according to the prior art are known as methods for recovering acrylic acid as solution from acrylic acid-containing gas with high selectivity. There is a difference in concentration of acrylic acid in a recovered solution depending on the method used particularly.

U.S. Pat. No. 3,932,500 discloses a process comprising absorbing acrylic acid from an acrylic acid-containing product gas with a high-boiling, hydrophobic organic solvent, recovering acrylic acid from the absorbed solution and recycling the solvent to an absorption column. In this process, the concentration of acrylic acid at the bottom the absorption column is as low as 6-15% by weight, the amount of water contained in the absorbed solution is about 5% by weight, and the concentration of acrylic acid in the off-gas from the absorption column is about 1%. This loss of acrylic acid (~1%) at the top of the absorption column is connected directly with process economy and is burdensome considering that acrylic acid should be treated in subsequent processes without loss. Especially, in processes with larger-scale production, the loss of acrylic acid will not be cost-efficient. In order to increase the absorption of acrylic acid, the flow rate of a solvent for absorption needs to be increased. In this case, however, the concentration of acrylic acid in a solution obtained from the bottom of the absorption column will be reduced so that the flow rate of the solvent to be separated from acrylic acid solution in subsequent processes will be increased, resulting in inefficiency.

Japanese Patent Publication No. Sho 51-25602 discloses a process that comprises absorbing an acrylic acid-containing reaction product gas with water and recycling some of nitrogen, oxygen and water discharged from an absorption column to a reactor in order to adjust the gas concentration required for catalytic oxidation (see FIG. 4). This process has an advantage in that the circulating supply of water required in the reactor is possible since acrylic acid is absorbed with water in the absorption column. Also, the concentration of acrylic acid at the bottom of the absorption column is 40-80% by weight, and generally 60-70% by weight. Furthermore, the loss of acrylic acid vented from the absorption column is lower than that of the above-described absorption process using the organic solvent.

Other methods for recovering (meth)acrylic acid include methods in which quenching with an acrylic acid-containing solution is combined with absorption using water, aqueous solution or organic solvent (e.g. EP 9,545 and U.S. Pat. Nos. 4,554,054 and 6,498,272). For example, acrylic acid-containing gas obtained by catalytic gas phase oxidation at a high temperature of between 150° C. and 200° C. is quenched with acrylic acid-containing solution having a temperature of between 60° C. and 150° C. Then, uncondensed gas is discharged and recovered in a subsequent step via absorption using a solvent. EP 9,545 discloses a method of recovering acrylic acid carried out in a discrete and sequential mode or an integral mode, which comprises a step of quenching of acrylic acid-containing gas and a step of absorption using water. In this method, the concentration of acrylic acid in aqueous acrylic acid solution at the bottom of the recovering system is as low as about 60% by weight.

SUMMARY OF THE INVENTION

Recovering (meth)acrylic acid from product gas obtained by the catalytic gas phase oxidation as high-concentration (meth)acrylic acid solution with high yield can reduce the amount of by-products and impurities to be treated in subsequent purification processes, thereby improving the cost efficiency of the recovering process. Considering the recent tendency to use a distillation process as general purification process for (meth)acrylic acid, reducing the amount of by-products and impurities in a distillation process consuming a large amount of energy can play an important role in improvement of cost efficiency of the process. Therefore, an object of the present invention is to provide a method for recovering (meth)acrylic acid with maximized concentration.

Meanwhile, although a quenching process provides (meth) acrylic acid with relatively high concentration, it is disadvantageous in that the concentration of the recovered (meth) acrylic acid solution varies with quenching temperatures and a significantly small amount of (meth)acrylic acid is recovered compared to an absorption process using a solvent. Additionally, because a quenching process alone cannot accomplish complete recovery of (meth)acrylic acid, it should be used together with an absorption process. Under these circumstances, high-concentration (meth)acrylic acid solution obtained by a quenching process is combined with (meth) acrylic acid solution with relatively low concentration, which is obtained by an absorption process, resulting in a drop in concentration of acrylic acid solution obtained by the overall process.

Therefore, another object of the present invention is to provide a method for recovering (meth)acrylic acid by using a quenching process combined with a distillation process, wherein (meth)acrylic acid is recovered as (meth)acrylic acid solution with a concentration higher than that of a (meth) acrylic acid solution obtained by a conventional (meth) acrylic acid recovering process using an organic solvent or water, so that energy and cost efficiency can be improved in purification processes.

To achieve the above objects, in one aspect, the present invention provides a method for producing (meth)acrylic acid comprising a process of recovering (meth)acrylic acid as aqueous (meth)acrylic acid solution from a (meth)acrylic acid-containing gas mixture produced by the catalytic gas phase oxidation of at least one reactant selected from the group consisting of propane, propylene, isobutylene and (meth)acrolein, wherein the recovering process comprises the steps of: (1) feeding the (meth)acrylic acid-containing gas mixture into a quenching tower and condensing it in the quenching tower so as to recover an aqueous (meth)acrylic acid solution from the bottom of the quenching tower, in which some of the recovered aqueous (meth)acrylic acid solution is recycled to the quenching tower so as to condense the (meth)acrylic acid-containing gas mixture; (2) passing the uncondensed part of the (meth)acrylic acid-containing gas mixture from the quenching tower to a distillation tower; and (3) heating the bottom of the distillation tower to separate water-containing impurity components from the uncondensed (meth)acrylic acid-containing gas mixture and to discharge them from the top of the distillation tower.

In another aspect, the present invention provides a system for recovering (meth)acrylic acid as aqueous (meth)acrylic acid solution from a (meth)acrylic acid-containing gas mixture produced by the catalytic gas phase oxidation of at least one reactant selected from the group consisting of propane, propylene, isobutylene and (meth)acrolein, the system comprising: a quenching tower for condensing the (meth)acrylic acid-containing gas mixture by using an aqueous (meth)acrylic acid solution recycled to the quenching tower, the quenching tower further comprising a line for discharging an aqueous (meth)acrylic acid solution recovered from the bottom of the quenching tower, and a line for recycling some of the recovered aqueous (meth)acrylic acid solution to the upper portion of the quenching tower; a line for passing the uncondensed part of the (meth)acrylic acid-containing gas mixture in the quenching tower through the top of the quenching tower to a distillation tower; a distillation tower for carrying out distillation of the uncondensed (meth)acrylic acid-containing gas mixture by heating the bottom of the distillation tower to separate water-containing impurity components from the gas mixture; and a line for passing an aqueous (meth)acrylic acid solution recovered from the bottom of the distillation tower to a subsequent process.

The inventive method for producing (meth)acrylic acid may further comprise, after the process of recovering (meth)acrylic acid as aqueous (meth)acrylic acid solution from the (meth)acrylic acid-containing gas mixture produced by catalytic gas phase oxidation, a water separation process, a process for separating low-boiling point components/high-boiling point components, a dimer decomposition process and the like.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
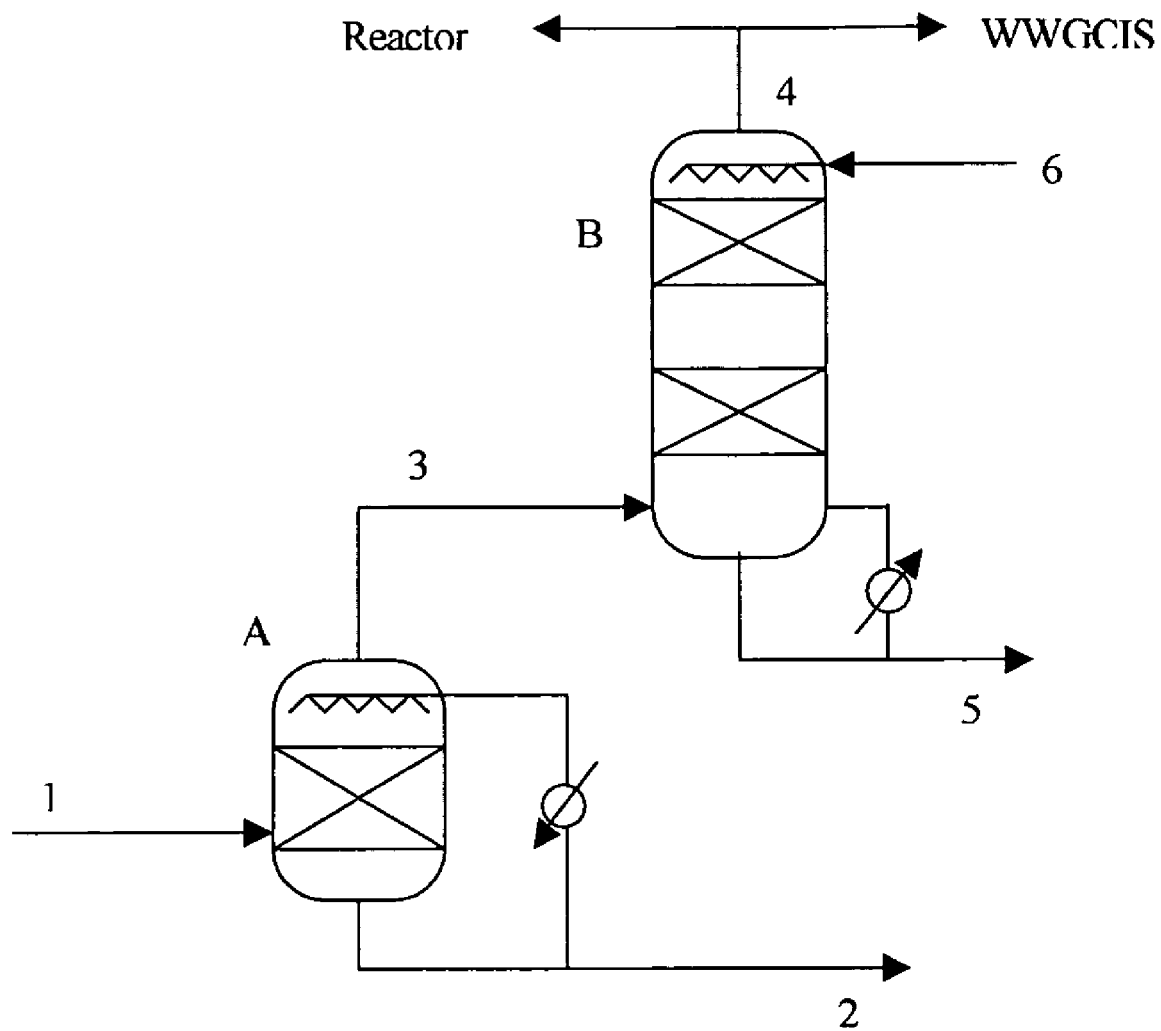
FIG. 1 is a schematic process diagram showing one embodiment of the present invention, wherein reference letter A is a quenching tower, B is a distillation tower, and C is a stripper, and reference numeral 1 is a line for feeding a reaction product gas, 2 is a line for discharging the bottom liquid of the quenching tower, 3 is a line for discharging an uncondensed gas from the quenching tower, 4 is a line for discharging gas from the distillation tower, 5 is a line for discharging the bottom liquid of the distillation tower, and 6 is a line for feeding water for controlling water content of the reactor.

Hereinafter, the method for producing (meth)acrylic acid in accordance with the present invention will be described in more detail.

(a) Process for Catalytic Gas Phase Oxidation of Propane, Propylene, Isobutylene and/or (Meth)Acrolein When propane, propylene, isobutylene and/or (meth)acrolein is catalytically oxidized in contact with oxygen or a molecular oxygen-containing gas, such as air, a (meth)acrylic acid-containing product gas can be obtained.

The catalytic oxidation is conventionally carried out in two stages. As the first-stage catalysts, materials allowing the gas phase oxidation of a propylene- or isobutylene-containing raw material gas and the production of (meth)acrolein as main product are used. As the second-stage catalysts, materials allowing the gas phase oxidation of (meth)acrolein-containing raw material gas and the production of (meth)acrylic acid as main product are used. The known first-stage catalysts are oxides containing iron, molybdenum and bismuth, and the second-stage catalysts contain vanadium as essential component. The temperature of the catalytic oxidation is generally in a range of 200-400° C.

In the case of production of acrylic acid from propane, propane is converted into propylene, propylene into acrolein, and acrolein into acrylic acid. In addition, there is another method for direct oxidation from propane to acrolein.

(b) Process in Quenching Tower

This is a process comprising: feeding the (meth)acrylic acid-containing gas mixture to the quenching tower A by line 1, and condensing the gas mixture in the quenching tower so as to recover an aqueous (meth)acrylic acid solution at the bottom of the quenching tower by line 2. In this process, some of the recovered aqueous (meth)acrylic acid solution is recycled to the upper portion of the quenching tower where it is used to condense the (meth)acrylic acid-containing gas mixture.

The (meth)acrylic acid-containing gas mixture contains a large amount of water vapor not only produced by the catalytic oxidation as by-product but also introduced into a reactor along with raw materials. Thus, when the (meth)acrylic acid-containing gas mixture is condensed in the quenching tower, some of the gas mixture will become an aqueous (meth)acrylic acid solution depending on thermodynamic properties such as temperature and pressure, and the remainder leaves out the quenching tower as it is. It is preferred that some of the recovered aqueous (meth)acrylic acid solution is recycled to the quenching tower with cooling so that it is used to adjust the temperature of vent gas from the quenching tower and to cool and condense the (meth)acrylic acid-containing gas mixture. In this regard, when the temperature of the quenching tower is increased, water contained in the gas mixture is less condensed, so that a relatively large amount of water can be evaporated, resulting in an aqueous solution with a high concentration of (meth)acrylic acid. If the temperature maintains low, a large amount of water will be condensed so that a small amount of water will be evaporated, resulting in an aqueous solution with lower concentration of (meth) acrylic acid.

The (meth)acrylic acid-containing gas mixture introduced into the quenching tower has a high temperature of 160-200° C. and thus can increase the temperature of the quenching tower. For this reason, it is preferred that the aqueous (meth) acrylic acid solution, which is recycled to the quenching tower, is cooled by heat exchange in order to maintain the temperature of the quenching tower.

The temperature of the condensed liquid in the quenching tower is maintained at a temperature of 65-80° C., and preferably 70-78° C. The temperature of less than 65° C. will result in an increase in the cooling load and will show difficulty in vaporizing water, and a temperature of more than 80° C. will cause the problem of polymerization of (meth)acrylic acid.

In substances obtained as by-products and impurities, the presence of (meth)acrolein is very critical. (Meth)acrolein which is produced mainly in the first-stage reaction for the oxidation of propylene or isobutylene is very excellent in the ability to be polymerized, and thus, even when it is present at a very small amount, it will be easily polymerized in a subsequent distillation process by heating, resulting in line blocking. Accordingly, it is preferred that not only (meth) acrolein but the remaining low boiling point impurities in an aqueous (meth)acrylic acid solution recovered at the bottom of the quenching tower are treated off by stripping, etc. The operation of the quenching tower at the highest possible temperature will allow the concentration of (meth)acrolein to be maintained at a low level, but as described above, make it difficult to recover (meth)acrylic acid. (Meth)acrolein in an aqueous (meth)acrylic acid solution at the bottom of the quenching tower, which is obtained at an operation condition of about 70° C., is about 400 ppm and can be completely removed by stripping, etc. After the (meth)acrolein is treated by stripping, (meth)acrolein and low-boiling point impurities such as water, unreacted raw materials, and gaseous by-products can be recycled to the top of the quenching tower or the gas inlet of the distillation tower so that they can be finally discharged through the top of the distillation tower to the outside of the system.

(c) Distillation Process

A gaseous mixture containing the remaining (meth)acrylic acid uncondensed in the quenching tower, water and inert gas such as nitrogen is discharged from the top of the quenching tower by line 3, and then is supplied to the distillation tower. While the bottom of the distillation tower is heated, impurities other than (meth)acrylic acid and uncondensed components are separated from the uncondensed (meth)acrylic acid-containing gas mixture at the top of the distillation tower. Due to the heat supplied from the bottom of the distillation tower, water contained in the uncondensed (meth)acrylic acid-containing gas mixture, which has a relatively high vapor pressure than (meth)acrylic acid, is evaporated preferentially, resulting in an increase in concentration of (meth)acrylic acid in the aqueous solution recovered from the bottom of the distillation tower.

A conventional process using a quenching tower combined with an absorption column is different from the method using a distillation tower according to the present invention in that there is no step of heating an absorption column for the purpose of distillation of water.

In order to heat the bottom of the distillation tower, direct heating methods using a kettle or siphon at the bottom of the distillation tower, or indirect heating methods using an external means (for example, a heat exchanger or reboiler) may be utilized.

The bottom temperature of the distillation tower depends on heat quantity supplied thereto. In general, the distillation tower is operated at a bottom temperature of between 68° C. and 85° C., preferably of 70° C. or higher, more preferably of between 72° C. and 78° C. It is possible to prevent polymerization of (meth)acrylic acid to a certain degree by introducing molecular oxygen and an inhibitor. However, it is inevitable that (meth)acrylic acid forms dimer and polymer as temperature increases. Therefore, the distillation tower should be operated at an adequate temperature determined by experimental observation. Since the polymerization inhibitor that may be used should be water-soluble in the presence of components in the distillation tower, any inhibitor may be used as long as it is soluble in water. In this regard, hydroquinone generally known to one skilled in the art is sufficient.

In general, when (meth)acrylic acid is recovered through an absorption process wherein water or an organic solvent is brought into contact with reaction product gas in a counter-current manner, the concentration of (meth)acrylic acid in the recovered solution is 40-70% by weight (for water) or 10-35% by weight (for an organic solvent). On the contrary, the concentration of (meth)acrylic acid in the aqueous solution obtained from the method using a quenching tower combined with bottom-heated distillation tower according to the present invention is 75-90% by weight. More particularly, it is possible to recover (meth)acrylic acid with a very high concentration in the form of the aqueous (meth)acrylic acid solution containing 75-90% by weight of (meth)acrylic acid, 1-4% by weight of acetic acid, 0.2-0.7% by weight of various high-boiling impurities and 8-20% by weight of water. Because the concentration of (meth)acrylic acid in the aqueous (meth)acrylic acid solution is increased according to the present invention, the amount of water as impurity to be treated in a subsequent step is reduced, resulting in saving of energy consumption needed to such treatment. Furthermore, various types of purifying processes may be selected. For example, when the amount of water in the aqueous (meth) acrylic acid solution is low, it is possible to recover (meth) acrylic acid directly through a crystallization process rather than a conventional distillation process and to select a process using membrane separation technique with very low energy consumption.

Meanwhile, during the evaporation of water with a lower boiling point than that of (meth)acrylic acid, caused by heating the bottom of the distillation tower for increasing concentration of (meth)acrylic acid in the aqueous solution in the bottom of the distillation tower, it is expected that (meth) acrylic acid having high affinity to water is also discharged from the top of the distillation tower along with water, resulting in loss of (meth)acrylic acid. To obtain high yield of (meth)acrylic acid from the (meth)acrylic acid-containing reaction product gas, the amount of (meth)acrylic acid discharged along with water should be decreased. To accomplish this, it is preferable that vaporous (meth)acrylic acid moving upwardly toward the top of the distillation tower is caused to be moved into liquid water, which is supplied from the top part of the distillation tower and is moving downwardly to the bottom of the distillation tower, via sufficient gas-liquid contact and mass transfer, so that the (meth)acrylic acid can be obtained as aqueous solution at the bottom of the distillation tower. Without such liquid supply to the top part of the distillation tower, the only means, i.e., heating at the bottom of the distillation tower while passing uncondensed gas upwardly from the bottom of the distillation tower cannot accomplish the mass transfer via gas-liquid contact. Therefore, it is preferable that a small amount of water is supplied to the top part of the distillation tower as reflux for constituting the distillation tower so that counter-current gas-liquid contact can be made while permitting distillation. Additionally, as described in Japanese Patent Publication No. Sho51-25602, uncondensed part of the gas discharged from the top of the distillation tower, which contains nitrogen, oxygen, unreacted propylene, isobutylene and (meth)acrolein, (meth) acrylic acid and water may be recycled to the reactor. Among those components, nitrogen and water are important. It is essential in a commercial production process that nitrogen supplied in a large amount is recycled. Additionally, water is one of the essential components of the catalytic oxidation, and thus one-pass water supply in the form of water vapor to reactor directly is not cost-efficient. Therefore, energy saving can be accomplished by using recycled water flow in a significant part of water supply. In this case, it is preferable to adjust the water content in the gas discharged from the top of the distillation tower to 15-30% by volume so as to provide a sufficient water supplying source. To satisfy this, water is supplemented at the top of the distillation tower to compensate for insufficient water supply by using the heat supplied from the distillation tower.

Although water supplied to the top of the distillation tower substantially returns to the reactor to serve to adjust water content, the recycled amount of water should not be excessively large. After calculating incoming and outgoing energy, heat quantity needed for vaporizing the water supplied to the top of the distillation tower ultimately results from the reboiler disposed at the bottom of the distillation tower and consumption of steam supplied to the reboiler. Therefore, in order to reduce consumption of steam, a suitable amount of water should be supplied. We have observed that the amount of water suitably ranges from 15 to 30% by volume of the gas flow discharged from the top of the distillation tower. It is more economically preferable that the amount of water ranges from 19 to 25% by volume of the gas flow discharged from the top of the distillation tower. Additionally, the temperature of the top of the distillation tower ranges from 55° C. to 68° C. so as to satisfy such water content.

Water contained in the aqueous solution recovered from the bottom of the distillation tower and that of the quenching tower is recovered by passing it through a subsequent water separation process. A part of the recovered water is subjected to conventional wastewater disposal or partially recycled to the distillation tower. Preferably, water supply to the top of the distillation tower is controlled in such a manner that the supplemented amount of water plus the amount of fresh processing water and recycled water can be present in the above volume percent range.

After operation of the distillation tower at the bottom temperature of 75° C., the top temperature is 60-68° C., water content in the off-gas is 20-25% by volume and acrylic acid concentration in the off-gas is 0.5-0.9% by volume, the top temperature varying with the amount of water.

The distillation tower that may be used includes a conventional plate tower, wetted-wall tower, packing tower, etc. Generally, a plate tower or packing tower is preferable, a packing tower being the most preferable.

In order to make sufficient gas-liquid contact, high-efficiency packing is used preferably. Various kinds of packing may be used for providing sufficient gas-liquid contact and non-limiting examples thereof include sheet-type packing such as gauze packing or Mellapak, grid-type packing such as Flexigid, random packing such as Raschig ring, Pall ring or Cascade mini ring, etc. Preferably, the packing is selected considering mass transfer, pressure gap between the top and bottom of the distillation tower, or the like. We have found that structured packings provide the most preferable results.

Aqueous (meth)acrylic acid solution in the bottom of the distillation tower essentially comprises (meth)acrylic acid, water, and a small amount of by-product impurities (e.g. acetic acid), and the particular composition depends on the bottom temperature. When the distillation tower is operated in the above range of bottom temperatures, (meth)acrolein, which tends to cause problems such as line blocking, is substantially discharged from the top of the distillation tower. The concentration of (meth)acrolein in the aqueous (meth) acrylic acid solution obtained from the bottom of the distillation tower is 100 ppm or less with the proviso that the bottom temperature of the distillation tower is 75° C. In this case, there is no need for treatment of low-boiling point materials (for example, treatment of the aqueous solution recovered from the bottom of the distillation tower by a stripper). To accomplish flexible operation depending on variations in operational conditions, it is possible to selectively use or skip a stripper based on the concentration of (meth)acrolein obtained by analytical works.

Then, the aqueous solution recovered from the bottom of the distillation tower as well as the aqueous solution obtained by treating the aqueous solution from the bottom of the quenching tower by a stripper can provide purified (meth) acrylic acid by subsequent (meth)acrylic acid purification processes, including water separation, light and heavy cuts separation, and thermal decomposition. These purification processes may be generally carried out by conventional methods.

Hereinafter, a kind of embodiment of the present invention will be described with reference to the accompanying drawings.

FIG. 1 is a schematic diagram showing a system for recovering (meth)acrylic acid as aqueous (meth)acrylic acid solution from a (meth)acrylic acid-containing gas mixture produced by catalytic gas phase oxidation, according to one embodiment of the present invention.

First, a reaction product gas obtained by the catalytic gas phase oxidation of propane, propylene, isobutylene and/or (meth)acrolein with molecular oxygen is fed to quenching tower A through line 1. The solution obtained from the bottom of the quenching tower is cooled in a heat exchanger in a forced-circulation manner and then subjected to recycling to the upper portion of the quenching tower so that hot reaction product gas can be cooled. Through line 2, an aqueous (meth) acrylic acid solution from the bottom of the quenching tower is passed to units for separating and purifying (meth)acrylic acid in subsequent processes. As the subsequent processes, stripping for low-boiling point impurities such as (meth)acrolein and/or aldehydes and separation methods for purifying (meth)acrylic acid, such as distillation, crystallization and membrane separation may be used.

The gas containing the remaining (meth)acrylic acid which has not been condensed in the quenching tower is passed to distillation tower B through line 3. To the top of the distillation tower, water is supplied through line 6 for controlling water content in the reactor, and inert and uncondensed gaseous mixture discharged from the distillation tower is recycled to the reactor through line 4 or passed to the waste gas catalytic incinerator system (WGCIS).

Water is discharged from the top of the distillation tower by heating the bottom of the distillation tower with a reboiler, thereby increasing the concentration of (meth)acrylic acid in the aqueous (meth)acrylic acid solution. The aqueous (meth)

acrylic acid solution obtained thereby is discharged through line 5 and passed to a subsequent (meth)acrylic acid purification process.

Figure 2:
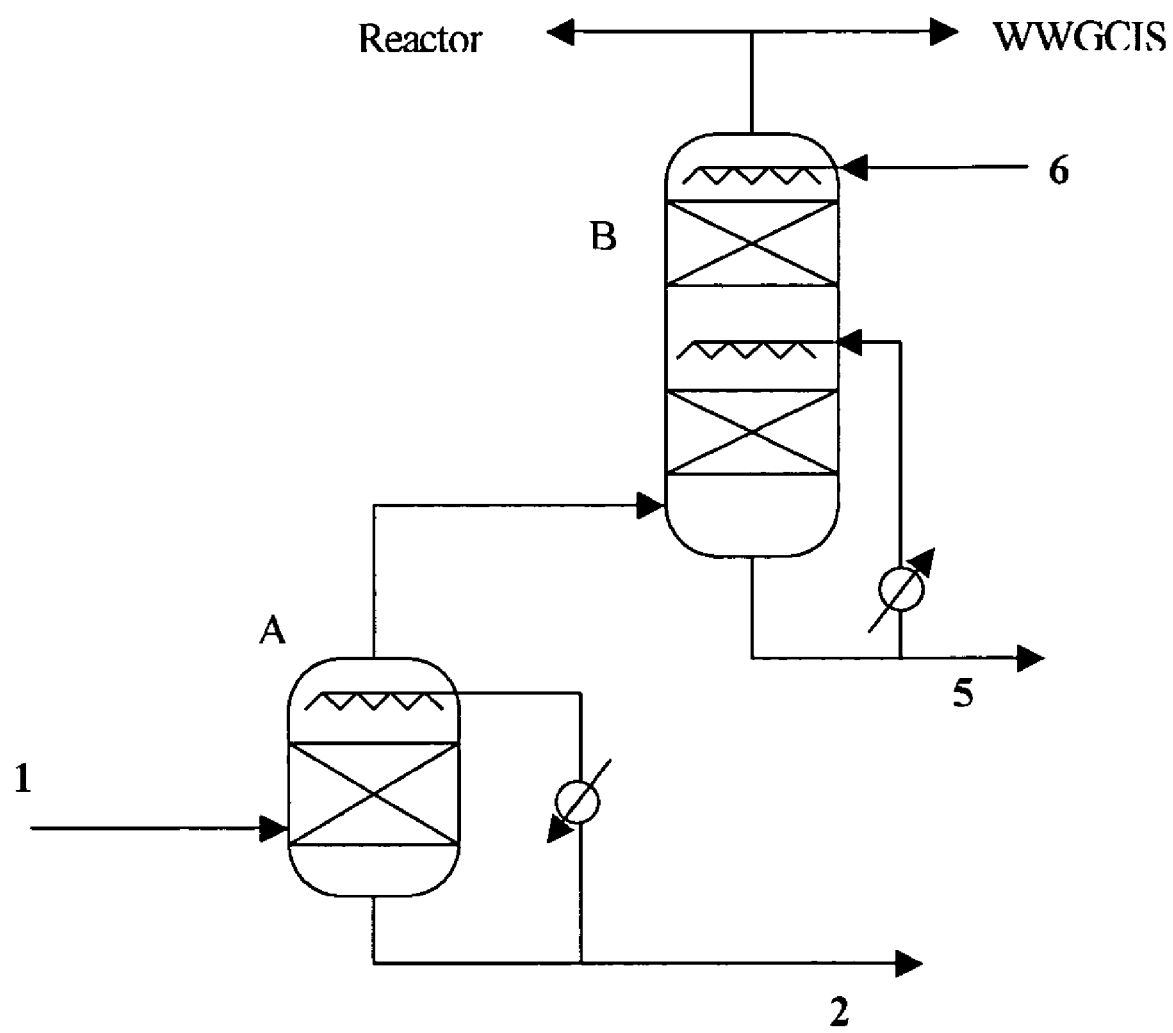
FIG. 2 is a process diagram showing an alternative embodiment of the present invention for increasing the concentration of (meth)acrylic acid in the distillation tower.

FIG. 2 illustrates an alternative embodiment for increasing the concentration of (meth)acrylic acid in the aqueous (meth) acrylic acid solution by enhancing evaporation of water in the distillation tower, wherein a part of the aqueous (meth)acrylic acid-containing solution, which is recovered from the bottom of the distillation tower, is partially discharged and another part thereof is recycled to any position of the distillation tower in the presence of heat supply.

Figure 3:
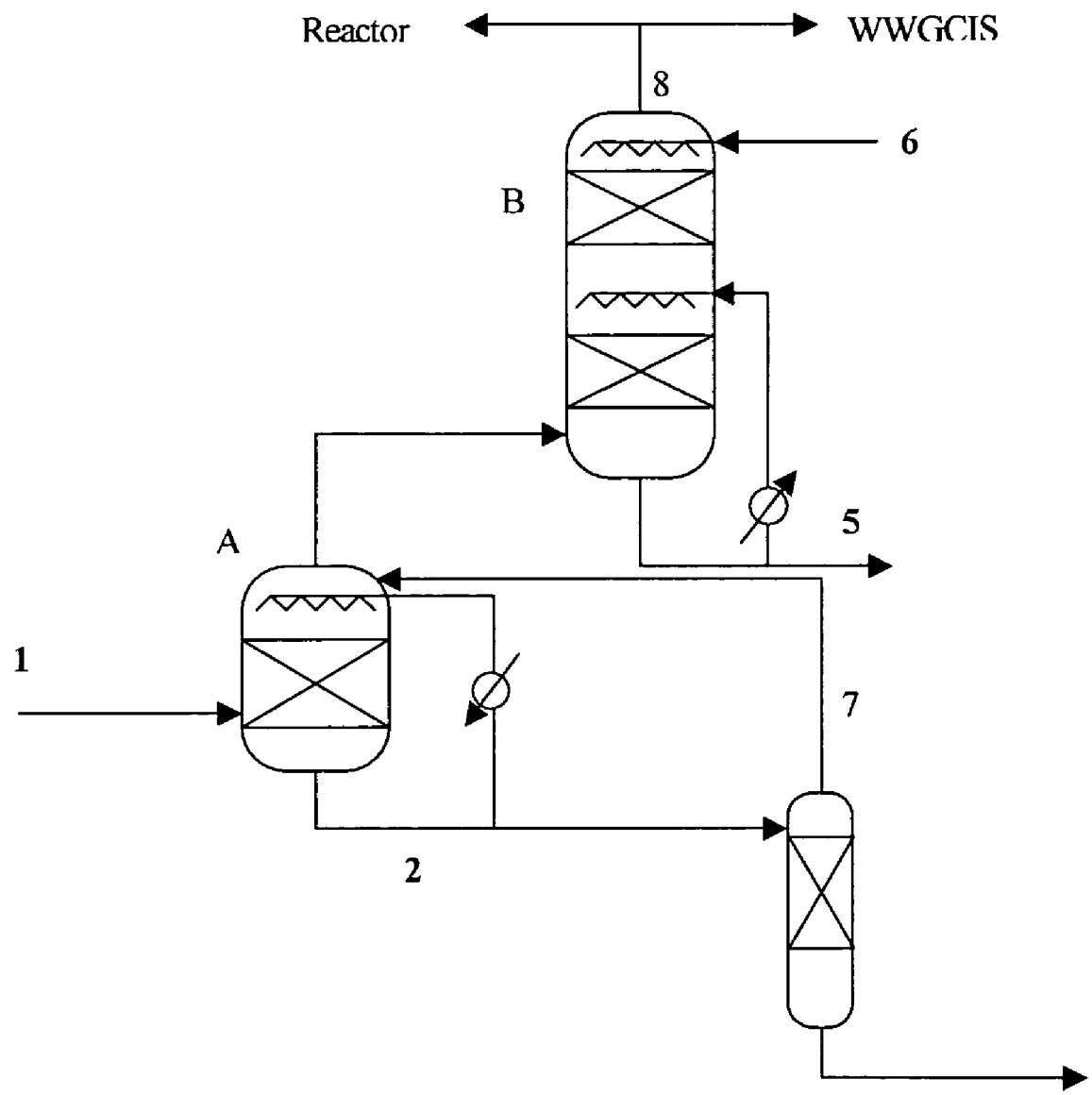
FIG. 3 is a process diagram showing another alternative embodiment of the present invention for removing (meth)acrolein from the aqueous (meth)acrylic acid solution recovered from the quenching tower.

FIG. 3 illustrates another alternative embodiment using treating unit C for removing low-boiling point materials such as (meth)acrolein from the aqueous (meth)acrylic acid solution recovered from the quenching tower. The flow discharged from treating unit C is recycled to the top part of the quenching tower through line 7 and then discharged to the outside of the system through line 8.

The embodiments in the drawings illustrate the respective methods, and these methods may also be performed in combination. Hereinafter, the present invention will be described in more detail by way of examples, but it is to be understood, however, that these examples are not construed to limit the scope of the present invention.

Comparative Example 1

Figure 4:
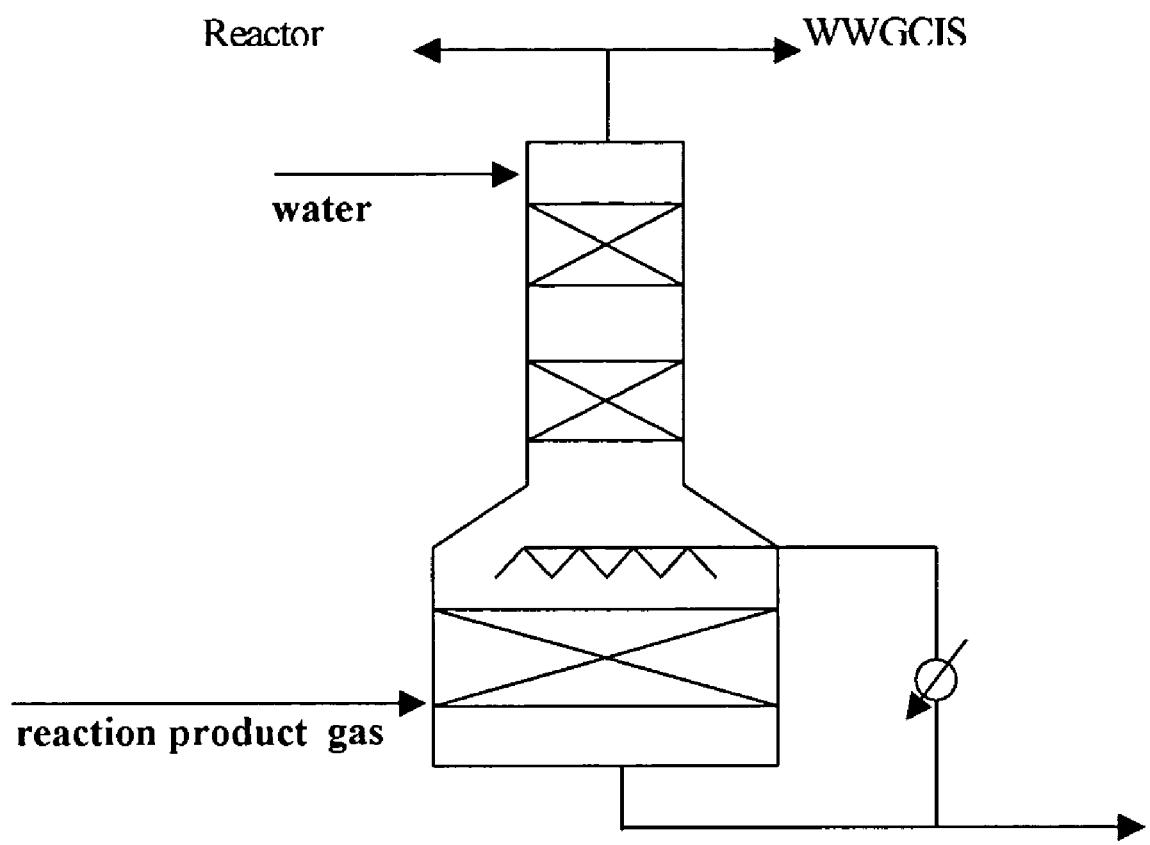
FIG. 4 shows a prior process for recovering (meth)acrylic acid using an absorption column.

A reaction product gas obtained by the catalytic gas phase oxidation of propylene with a molecular oxygen-containing gas was introduced into a conventional absorption column as shown in FIG. 4 and acrylic acid contained therein was absorbed and collected by using water. The composition of the reaction product gas consisted of 70.5% by weight of uncondensed components of nitrogen+oxygen, 1.5% by weight of unreacted propylene+propane, 2.8% by weight of carbon dioxide+carbon monoxide, 9.5% by weight of water, 14.5% by weight of acrylic acid, and the remainder of other condensable components.

As absorption column unit, a tray column with an internal diameter of 200 mm was used, and the reaction product gas was cooled to 170° C. with a heat exchanger placed on the exit line of an oxidation reactor and fed to the bottom of the absorption column. The acrylic acid-containing solution obtained from the column bottom was circulated to the fifth stage from the bottom through a line on which the external heat exchanger for cooling the circulating solution was placed. The column consisted of a total of 25 stages, and water with a temperature of 55° C. was fed to the top of the column. The absorption column was operated at a top temperature of 60° C. under a pressure of 1050 mmH$_2$O. At the top of the absorption column, 70% by weight of water based on the weight of acrylic acid contained in the reaction product gas was introduced to absorb the acrylic acid. The composition of the aqueous acrylic acid solution at the column bottom, which had been recovered as described above, contained 61.8% by weight of acrylic acid, the loss of acrylic acid to the top of the column was 1.8% by volume, and water content was 18.4% by volume.

Example 1

A reaction product gas of acrylic acid with the same composition as illustrated in Comparative Example 1 was used. As quenching tower, an SUS ring-packed drum with a diameter of 300 mm and a height of 80 mm was used, and a portion of the solution at the bottom of the quenching tower was circulated to the top of the quenching tower through a line on which a heat exchanger was placed so that the temperature of the solution at the column bottom reached 72° C. The composition of gas discharged from the top of the quenching tower consisted of 82.5% by weight of nitrogen+oxygen, 12.5% by weight of acrylic acid, 9.8% by weight of water and the balance amount of impurities, and had a temperature of 61.5° C. The gas discharged from the quenching tower was passed through an insulated line to a distillation tower. As the distillation tower, a gauze-packed column, which has a diameter of 200 mm and a height of 1350 mm, similar with one illustrated in Comparative Example 1 was used. To the top part of the distillation tower, water was supplied at 55° C. Particularly, the water supply was controlled so that the water content in the gas discharged from the top of the distillation tower, which was collected and analyzed during the operation of the system, can be 24% by volume. The top temperature and pressure in the distillation tower were set to 65° C. and 1050 mmH$_2$O, respectively. A 3 L flask was placed at the bottom of the distillation tower and the flask was heated to adjust the temperature of the bottom liquid to 75° C. The composition of the aqueous acrylic acid solution recovered from the bottom of the quenching tower contained 79.2% by weight of acrylic acid and that recovered from the bottom of the distillation tower contained 72% by weight of acrylic acid. Additionally, the gas discharged from the top of the distillation tower contained 0.9% by volume of acrylic acid.

Example 2

Example 1 was repeated, except that the aqueous acrylic acid solution was pumped out from the flask placed at the bottom of the distillation tower, heated to 80° C. by using a heat exchanger, and 75% by weight of the solution was recycled to the cascade mini ring layer packed to a height of 50 cm from the bottom of the distillation tower. The top temperature of the distillation tower was 66° C. Concentration of acrylic acid in the off-gas was 1.1% by volume, and that in the aqueous acrylic acid solution recovered from the bottom of the distillation tower was 75% by weight.

INDUSTRIAL APPLICABILITY

As described above, according to the inventive method for producing (meth)acrylic acid by using a quenching process combined with a distillation process while heating the bottom of the distillation tower, it is possible to recover (meth)acrylic acid as aqueous solution containing (meth)acrylic acid in a higher concentration compared to a (meth)acrylic acid solution obtained by a conventional method for recovering (meth) acrylic acid by using an organic solvent or water, resulting in a reduction in the cost of operating energy and equipment investment for the subsequent separation processes. This allows the (meth)acrylic acid production process to be efficient and economic.

What is claimed is:

1. A method for producing (meth)acrylic acid comprising a process of recovering (meth)acrylic acid as aqueous (meth) acrylic acid solution from a (meth)acrylic acid-containing gas mixture produced by the catalytic gas phase oxidation of at least one reactant selected from the group consisting of propane, propylene, isobutylene and (meth)acrolein, wherein the recovering process comprises the steps of:

(1) feeding the (meth)acrylic acid-containing gas mixture into a quenching tower and condensing it in the quenching tower so as to recover an aqueous (meth)acrylic acid solution from the bottom of the quenching tower, in which some of the recovered aqueous (meth)acrylic acid solution is recycled to upper portion of the quenching tower so as to condense the (meth)acrylic acid containing gas mixture;

(2) passing the uncondensed part of the (meth)acrylic acid containing gas mixture from the top of the quenching tower to a distillation tower; and (3) heating the bottom of the distillation tower to separate water-containing impurity components from the uncondensed (meth)acrylic acid-containing gas mixture and to discharge them from the top of the distillation tower, and recovering a (meth)acrylic acid solution from the bottom of the distillation tower.

2. The method as claimed in claim 1, wherein the temperature of the solution condensed in the quenching tower ranges from 65° C. to 85° C.

3. The method as claimed in claim 1, wherein the temperature of the bottom of the distillation tower ranges from 68° C. to 85° C.

4. The method as claimed in claim 1, wherein a small amount of water is supplied to the top part of the distillation tower as reflux so as to make countercurrent gas liquid contact that permits distillation in the distillation tower.

5. The method as claimed in claim 4, wherein the amount of water supplied to the top part of the distillation tower is controlled in such a manner that the water content in the gas discharged from the top of the distillation tower is 15-30% by volume.

6. The method as claimed in claim 1, wherein a part of the aqueous (meth)acrylic acid solution discharged from the bottom of the distillation tower is heated and recycled to any point of the distillation tower.

7. The method as claimed in claim 1, wherein the concentration of (meth)acrylic acid in the aqueous (meth)acrylic acid solution obtained from the quenching tower is 75% or higher and the concentration of (meth)acrylic acid in the aqueous (meth)acrylic acid solution obtained from the distillation tower is 65% or higher.

8. The method as claimed in claim 1, wherein the temperature of the top of the distillation tower ranges from 55° C. to 68° C.

9. The method as claimed in claim 1, wherein the aqueous (meth)acrylic acid solution recycled to the quenching tower in step (1) is cooled by heat exchange.

10. The method as claimed in claim 1, wherein either or both of the (meth)acrylic acid solution recovered from the bottom of the quenching tower and the (meth)acrylic acid solution recovered from the bottom of the distillation tower are treated by a stripper to separate (meth) acrolein.

11. The method as claimed in claim 10, wherein a gas treated by the stripper and discharged from the stripper is supplied to the quenching tower or distillation tower in a condensed or uncondensed state.

12. A system for recovering (meth)acrylic acid as an aqueous (meth)acrylic acid solution from a (meth)acrylic acid-containing gas mixture produced by the catalytic gas phase oxidation of at least one reactant selected from the group consisting of propane, propylene, isobutylene and (meth)acrolein, the system comprising:

a quenching tower for condensing the (meth)acrylic acid containing gas mixture by using an aqueous (meth) acrylic acid solution recycled to the quenching tower, the quenching tower further comprising a line for discharging an aqueous (meth)acrylic acid solution recovered from the bottom of the quenching tower, and a line for recycling some of the recovered aqueous (meth) acrylic acid solution to the upper portion of the quenching tower;

a line for passing the uncondensed part of the (meth)acrylic acid-containing gas mixture in the quenching tower through the top of the quenching tower to a distillation tower;

a distillation tower for carrying out distillation of the uncondensed (meth)acrylic acid-containing gas mixture by heating the bottom of the distillation tower to separate water-containing impurity components from the gas mixture; and a line for passing an aqueous (meth)acrylic acid solution recovered from the bottom of the distillation tower to a subsequent purification process, wherein the line for passing an aqueous (meth)acrylic acid solution recovered from the bottom of the distillation tower passes to the subsequent purification process, passes through a stripper for treating the aqueous solution from the bottom of the quenching tower prior to passing to the purification process, or both, and wherein the purification process is selected from the group consisting of water separation, light and heavy cuts separation, and thermal decomposition.

* * * * *